(12) United States Patent
Buolamwini (10) Patent No.: US 7,582,616 B2
(45) Date of Patent: Sep. 1, 2009

(54) NUCLEOSIDE TRANSPORT INHIBITORS

(75) Inventor: John Kwesi Buolamwini, Cordova, TN (US)

(73) Assignee: Quesrema Enterprises LLC, Cordova, TN (US)

( * ) Notice: Subject to any disclaimer, the term of this patent is extended or adjusted under 35 U.S.C. 154(b) by 277 days.

(21) Appl. No.: 10/558,176

(22) PCT Filed: Dec. 31, 2003

(86) PCT No.: PCT/US03/41686

§ 371 (c)(1),
(2), (4) Date: Aug. 6, 2007

(87) PCT Pub. No.: WO2004/060902

PCT Pub. Date: Jul. 22, 2004

(65) Prior Publication Data

US 2007/0293444 A1    Dec. 20, 2007

(51) Int. Cl.
*A01N 43/04* (2006.01)
*A61K 31/70* (2006.01)

(52) U.S. Cl. .............................. 514/45; 514/43; 514/47; 514/48

(58) Field of Classification Search ....................... None
See application file for complete search history.

(56) References Cited

OTHER PUBLICATIONS

Li et al. Anal. Chem. (2002), vol. 74, pp. 2573-2577.*

* cited by examiner

*Primary Examiner*—Patrick T Lewis (57) ABSTRACT

Compounds or compositions that are inhibitors and/or ligands of nucleoside transporters; and methods of treating cancer, heart disease and stroke, as well as AIDS and other infectious diseases.

13 Claims, 1 Drawing Sheet

NUCLEOSIDE TRANSPORT INHIBITORS

FIELD OF THE INVENTION

The present invention relates to the field of compounds that bind to the cellular nucleoside uptake proteins termed nucleoside transporters. The compounds help prevent in vivo metabolic inactivation and production of toxic metabolites that is associated with the available related nucleoside transport inhibitors. These compounds are thus novel therapeutic agents in cancer, heart disease and stroke, as well as AIDS and other infectious diseases.

BACKGROUND OF THE INVENTION

Mammalian cells take up, and release physiological nucleosides and many of their synthetic analogs primarily by means of specific integral plasma membrane glycoproteins known as nucleoside transporters (Paterson and Cass, 1986; Plagemann et al., 1988; Gati and Paterson, 1989; Paterson et al., 1991; Cass, 1995; Thorn and Jarvis, 1996). Nucleoside transporters have been classified into two categories: (i) equilibrative (facilitated diffusion) and (ii) concentrative (secondary active) sodium-dependent. Two equilibrative transporters with similar broad substrate specificities have been identified and designated as the es (equilibrative sensitive) and ei (equilibrative insensitive) transporters, on the basis of their sensitivity or insensitivity to inhibition by nitrobenzylthioinosine (NBMPR, 1), respectively. Six sodium ion-coupled (concentrative) transporters designated cif/N1, cit/N2, cib/N3, cit/N4, cs/N5 and csg/N6 have also been identified in mammalian tissues (Cass, 1995, Young et al., 2000). However, sodium-dependent nucleoside transport is only a minor component of mammalian tissues and plays a role mainly in secretory tissues. The es transporter is by far the major nucleoside transporter of most mammalian tissues, especially heart tissue (Williams, 1996; Hoehner et al., 1996; Abd-Elfattah et al., 1998a), and is highly sensitive to inhibition by NBMPR, and related purine 6-position (nitrobenzyl) nucleosides (Paul et al., 1975; Robins et al., 1994; Paterson et al., 1983), and has a high affinity for NBMPR ($K_d$ in the 0.1-1.0 nM range).

1, NBMPR

In addition to their role as precursors for salvage synthesis of nucleotides used for DNA and RNA synthesis, physiological nucleosides are also involved in signal transduction and metabolic pathways. Adenosine is especially involved in protecting tissues from ischemic and inflammatory damage (Engler, 1987; Ohta and Sitkovsky, 2001). Adenosine's tissue protective effects can be harnessed for the treatment of ischemic heart disease and stroke, as wells as other ischemic conditions and the preservation of donor hearts and kidneys (reviewed in Buolamwini, 1997). Agents that potentiate endogenous adenosine's protective effects are therefore being pursued. One attractive potential strategy for in vivo adenosine potentiation is adenosine transport blockade (Van Belle, 1993a, 1993b). Adenosine is automatically released endogenously in myocardial infarction or stroke, as a "retaliatory" metabolite (Newby, 1984) through ATP catabolism to protect against ischemic tissue damage through its interaction with cell surface G-protein coupled adenosine receptors (Ver Donck, 1994; Linden, 2001). However, adenosine's protective effects are quickly lost mainly by cellular uptake through nucleoside transporters (Van Belle, 1993a), which contribute to its depletion from the extracellular milieu. The adenosine potentiation effects of nucleoside transporter inhibitors, which help maintain extracellular adenosine concentrations, have been demonstrated in heart and brain ischemia models (Van Belle, 1993a, 1993b; Abd Elfattah and Wechsler, 1994; Abd-Elfattah et al., 1998b; Rudolphi et al., 1992; Parlinson et al., 2000; Zhang et al., 2002). The benefit of using NT inhibitors rather than adenosine receptor agonists is that the effects of NT inhibitors, unlike adenosine receptor agonists are localized (Van Belle, 1993b) to tissues where adenosine is released locally in an ischemic episode, making this approach event- and site-specific. Adenosine receptor agonists on the other hand will trigger adenosine receptors all over the body leading to unwanted side effects, a major limitation in the drug development of adenosine receptor agonists (Erion, 1993). Other less attractive adenosine enhancement strategies include the use of adenosine deaminase (ADA) inhibitors such as deoxycoformycin (Phillis and O'Regan, 1996). The disadvantage in using ADA inhibitors is that they are prone to cause severe combined immunodeficiency (SCID), a condition that is observed in a genetic deficiency in the production of the enzyme (Strachan and Read, 1996).

The combination of NT inhibitors with de novo synthesis inhibitor antimetabolite chemotherapy in cancer and infectious diseases is also of considerable interest (Buolamwini, 1997). Thus, dipyridamole has been shown to enhance the antitumor effects of methotrexate (Cabral et al., 1984) and 5-fluorouracil (Grem and Fischer, 1985). The experimental and clinical studies relating to the modulation of 5-fluorouracil by nucleoside transport inhibitors have been reviewed (Tew et al., 1993). The continued interest in this therapeutic approach is shown by a recent prospective randomized clinical trial that tested the efficacy of a combination of orally administered dipyridamole with leucovorin and 5-FU in advanced colorectal cancer (Kohne et al., 1995).

The available NT inhibitors, however, lack the requisite pharmacological profiles are toxic, mutagenic, ineffective in vivo, or nonspecific (reviewed in Buolamwini, 1997), and therefore the above-mentioned therapeutic strategies will benefit tremendously from the discovery of better nucleoside transport inhibitors.

In this regard, the compounds that are the subject of this disclosure are invented to accomplish two goals: (i) to provide conformationally restrained analogs of NBMPR to be used as probes of the bioactive conformation of NBMPR for better rational nucleoside transporter inhibitor design and (ii) to overcome a major disadvantage of NBMPR, which has to do with the lability of the $S^6$-nitrobenzyl substituent, which is easily lost in vivo to drastically reduce NT inhibitory activity (up to a 1000 fold). This lability has actually allowed NBMPR to be used as an effective photolabeling reagent for the es nucleoside transporter (Young et al., 1983; Boumah et al., 1992). Incorporating the high potency conferring nitrobenzyl group of NBMPR into a nitrotetrahydroisoquinoline system prevents it from being easily cleaved. At the same time this molecular modification restrains the conformational flexibility at the purine 6-position substituents and helps to better map the orientation of the nitrobenzyl group when bound to the es transporter.

Novel compounds are synthesized and their binding affinity at the es nucleoside transporter evaluated by a flow cytometric assay (Buolamwini et al., 1994). Their inhibition of nucleoside uptake has also been demonstrated, as well as their ability to enhance the recovery of isolated heart preparation from global ischemia.

SUMMARY OF THE INVENTION

The present invention is directed to compounds or compositions that are inhibitors and/or ligands of nucleoside transporters for research and therapeutic uses. These compounds include four isomeric aromatic nitro-1,2,3,4-tetrahydroisoquinolinylpurine ribosides and appropriate derivatives thereof.

The present invention includes, but is not limited to, the following compounds, as well as analogs thereof:

FORMULA I wherein:
$X_1$-$X_9$ are each independently C, N, provided that where X is N, the R substituent is absent;
Y is O, S, NH, $CH_2$;
$R_1$ is H, OH, $NH_2$, $N_3$, halogen;
$R_2$ is H, OH, $NH_2$, $N_3$, halogen;
$R_3$ is H, $NH_2$, substituted amino, halogen;
$R_4$ is H, OH, $NO_2$, CN, $N_3$, NCS, halogen;
$R_5$ is H, OH, $NO_2$, CN, $N_3$, NCS, halogen, halogen-$CH_2COCH_3$;
$R_6$ is H, OH, $NO_2$, CN, $N_3$, NCS, halogen, halogen-$CH_2COCH_3$;
$R_7$ is H, OH, $NO_2$, CN, $N_3$, NCS, halogen;
$R_9$ is H, OH, $NH_2$, $N_3$, halogen;
$R_8$ is H, OH, $OCH_3$, $NO_2$, CN, $N_3$, NCS, halogen, A-Reporter (where A is O, S, NH, and the Reporter is a tethered reporter group;
$R_{10}$ is H, OH, $NH_2$, $N_3$, halogen;
provided that when $X_1$-$X_4$, $X_6$, are all C, $X_5$, $X_7$, $X_8$, $X_9$ are all N, and Y is O, substituents $R_4$, $R_5$, $R_6$, $R_7$, cannot all be H at the same time if $R_1$ is H, $R_2$ is OH, $R_3$ is H and $R_8$ is OH.

Other embodiments of the present invention include the following compounds and analogs thereof:

FORMULA II $R_1$ = H, OH, Halogen
$R_2$ = H, OH, Halogen
$R_3$ = H, $NH_2$ or substituted amino, Halogen
$R_4$ = H, OH, $NO_2$, CN, $N_3$, NCS, Halogen
$R_5$ = H, OH, $NO_2$, X, CN, $N_3$, NCS,
  X—$CH_2COCH_3$ (where X is Cl, Br, or I)
$R_6$ = H, OH, $NO_2$, X, CN, $N_3$, NCS,
  X—$CH_2COCH_3$ (where X is Cl, Br, or I)
$R_7$ = H, $NO_2$, OH, CN, $N_3$, NCS, Halogen
$R_8$ = H, OH, $OCH_3$, $NO_2$, CN, $N_3$, NCS, Halogen, A-Reporter
  (where A is O, S, NH and the Reporter is a tethered reporter group such as a fluorophore (fluorescein, texas red, Cy3, Cy5, Bodipy, phycoerythrin or other fluorophore), biotin, or radioactive group provided that substituents $R_4$, $R_5$, $R_6$, $R_7$, cannot all be H at the same time if $R_1$ is H, $R_2$ is OH, $R_3$ is H and $R_8$ is OH.

The present invention also comprises pharmaceutical formulations of the above compounds, including pharmaceutically acceptable acid addition salts, esters, or prodrugs thereof.

The present invention also relates to methods of treating cancer, heart disease, strokes, AIDS, and infectious diseases comprising administering a compound or composition of the present invention to a subject in need thereof.

DETAILED DESCRIPTION OF THE INVENTION

As stated above, the present invention relates to nucleoside transport inhibitors.

In other embodiments of the present invention, the present invention is directed to the following compounds and analogs thereof:

wherein R$_1$ and R$_2$ are described above.

In other embodiments, the present invention is directed to the following compounds and analogs thereof:

The present invention also comprises pharmaceutical compositions/formulations of all the compounds of the present invention, including pharmaceutically acceptable acid addition salts, esters, or prodrugs thereof. Compounds of the invention and their physiologically acceptable salts may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient. While it is possible for the active ingredients to be administered alone it is preferably to present them as pharmaceutical formulations. The formulations, both for veterinary and for human use, of the present invention comprise at least one active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof.

As stated above, the present invention also relates to methods of treating cancer, heart disease, strokes, AIDS-related diseases, and infectious diseases comprising administering a compound or composition of the present invention to a subject in need thereof.

Examples of forms of cancers particularly suitable for treatment with the compounds of the present invention are malignant melanoma, cervical cancer, breast cancer, colorectal cancer, color cancer, cancer of the head and neck, gastric cancer, renal cancer, laryngeal cancer, rectal cancer, non-Hodgkins lymphoma and leukemias.

The compounds of the present invention may be used to treat and inhibit heart disease and strokes, including ischemic heart disease and stroke, as well as ischemic conditions of kidney and liver, thereby allowing the preservation of these organs for transplant purposes.

According to a further aspect of the present invention provides for the use of the compounds of the present invention for the treatment and/or prophylaxis of acute and chronic infectious diseases. Examples of acute viral infections are: Herpes viruses, influenza viruses, parainfluenza viruses, adenoviruses, coxsakie viruses, picorna viruses, rotaviruses, hepatitis (A, B, C, D) virus, mumps virus, rubella virus, measles virus, pox viruses, respiratory syncytial viruses, papilloma viruses, and enteroviruses, arenavirus, rhinoviruses, poliovirus, Newcastle disease virus, rabies virus, arboviruses. Examples of chronic viral infections are: persistent herpes virus infections, Epstein Barr virus infection, persistent rubella infections, papovirus infections, hepatitis virus infections and human immunodeficiency virus infection.

The compounds of the invention may be used in the treatment or prophylaxis of retroviral, gram-negative bacterial, fungal and protozoal infections and in the manufacture of a medicament for the treatment or prophylaxis of a retroviral, gram-negative bacterial, fungal and protozoal infection. Examples of bacteria include: *Escherichia coli, Salmonella dublin, Salmonella typhosa, Salmonella typhimurium, Shigella flexneri, Citrobacter freundii, Klebsiella pneumoniae, Vibrio cholerae, Vibrio anquillarum, Enterobacter aerogenes, Pasteurella multocida, Haemophilus influenzae, Yersinia enterocolitica, Pasteurella haemolytica, Proteus mirabilis* and *Proteus vulgaris*, the causative organisms of such ailments as travellers' diarrhoea, urinary tract infections, shigellosis, typhoid fever and cholera in humans, as well as animal diseases such as calf neonatal enteritis, pig post-weaning enteritis and chicken colisepticaemia. Examples of fungi include *Candida, Aspergilus* and *pneumocistis carinii*. Examples of protozoa include *Plasmodium, Giadia,* and *Toxoplasma.*

As stated above, the compounds of the present invention may be, or may be part of an effective treatment or preventative against AIDS-opportunistic diseases, including the following viruses: human T-cell lymphotropic viruses (HTLV), especially HTLV-I, HTLV-II and HTLV-III (HIV); feline leukaemia virus, equine infectious anaemia virus, caprine arthritis virus and other lentiviruses, as well as other human viruses such as hepatitis B virus, Epstein-Barr virus (EBV) and the causative agent of multiple sclerosis (MS).

The activity of the compounds according to the invention against such a wide range of bacterial, fungal, protozoal and viral infections is clearly of great advantage in medicine, and the novel mode of action allows the use of these compounds either alone or in combination therapy with know agents to reduce the chance of resistance developing. The compounds of the present invention may be used in the combination therapy with known medicaments, as the compounds of U.S. Pat. No. 5,064,946, incorporated herein by reference.

The amounts required of the active ingredient will depend upon a number of factors including the severity of the condition to be treated and the identity of the recipient and will ultimately be at the discretion of the attendant physician or veterinarian.

EXAMPLES

The following Examples show how to make and use the present invention. The specific compounds set forth herein are for exemplary purposes only and are not intended to limit the scope of the present invention in any way.

Example 1

This example shows how to make example compounds of the present invention. More specifically, this example demonstrates how to make four aromatic nitro isomers of 6-position nitro-1,2,3,4-tetrahydroisoquinolinylpurine ribosides NBMPR analogues (compounds 2-5). Several literature methods are employed to synthesize the required nitro-1,2,3,4-tetrahydroisoquinoline (compounds 6-9), which are subsequently reacted with the commercially available 6-chloropurine riboside (10) according to Scheme 1 to obtain the target compounds. The commercially available 5-nitroisoquinoline (11) is reduced using sodium borohydride in ethanol to afford the 5-tetrahydroisoquinoline (6) intermediate in good yield (about 90%). The 7-nitrotetrahydroisoquinoline intermediate (8) is prepared in about 50% yield by nitration of the commercially available 1,2,3,4-tetrahydroisoquinoline using $KNO_3$ in concentrated sulfuric acid according to the method of Ajao et al. (1985) (Scheme 3). The 6- and 8-nitro-1,2,3,4-tetrahydroisoquinoline intermediates 7 and 9, are prepared following reaction Scheme 4 according to the report by Tercel et al. (1996) as follows.

Scheme 1

6, 5-nitro
7, 6-nitro
8, 7-nitro
9, 8-nitro

+

10

2, 5-nitro
3, 6-nitro
4, 7-nitro
5, 8-nitro a, $CaCO_3$/Ethanol

Scheme 2

11    6 a, $NaBH_4$/EtOH, 0° C.

Scheme 3

12    8 a, $KNO_3$/Conc. $H_2SO_4$, 5° C.

Scheme 4

8    13    14    15

Reagents and conditions:
a, (Ac)₂O/Et₃N, CH₂Cl₂; b, NH₂NH₂•xH₂O/FeCl₃•6H₂O/Activated carbon/MeOH/reflux; c, TFA/CH₂Cl₂; d, KNO₃/conc. H₂SO₄; e, HCl/MeOH, reflux; f, NaNO₂/HCl, H₃PO₂; g, conc. HCl/MeoH, reflux The 7-nitro-1,2,3,4-tetrahydroisoquinoline intermediate (8) used to synthesize compound 4 (see Scheme 2) is protected by acetylation to give compound 13. The $NO_2$ group of 13 is reduced to an $NH_2$ group to obtain compound 14. The $NH_2$ group of 14 is subsequently protected and the resulting compound 15 is nitrated to afford the nitro compounds 16 and 17. Compounds 16 and 17 are deprotected to give free $NH_2$ substituted compounds 18 and 19, which are subjected to diazotization using $NaNO_2$ and HCl in the presence of $H_3PO_3$ to replace the $NH_2$ by H, to obtain compounds 20 and 21. Compounds 21 and 22 are deprotected to obtain the required intermediates 7 and 9. Compound 22, which is the analog of compounds 2-5 without the nitro substituents, is also synthesized and tested for comparison. Its synthesis is achieved by reacting compound 8 with compound 10 according to the reaction in Scheme 1.

The results show that these compounds are able to bind to the es transporter in K562 cells with different affinities. Compound 3 is the most tightly bound to the transporter, among the new compounds, being bound as tightly as the prototype compound, NBMPR (see FIG. 1). Compound 4 followed it, which also has $IC_{50}$ value in the low nanomolar range see FIG. 1). Compounds 2 and 5 are much less potent inhibitors of SAENTA-fluor binding to the es transporter compared to compounds 3 and 4.

Example 2

Experimental

Chemistry. Thin-layer chromatography (TLC) is conducted on silica gel $F_{254}$ plates (Analtech). Compounds are visualized by UV light or 5% $H_2SO_4$ in EtOH spraying reagent. $^1H$, $^{13}C$ spectra are recorded on Bruker ARX (300 MHz) instruments, using $CDCl_3$, $CD_3OD$, $(CD_3)_2SO$ or $CD_3COCD_3$ as solvents and tetramethylsilane (TMS) as internal standard. Flash column chromatography is performed on Fisher silica gel (170-400 mesh). Melting points are determined using a Fisher-Johns Melting Point Apparatus and are reported uncorrected. Mass spectra are obtained on a Bruker-HP Esquire-LC mass spectrometer, and IR spectra in KBr with a Perkin Elmer (System 2000 FT-IR) spectrometer. All solvents and reagents are bought from Aldrich and used without further purification.

Example 3

General Method for Preparation of Compounds 2, 3, 4, 5, 22

A mixture of 6-chloropurine riboside (10, 100 mg, 0.35 mmol), (mono-$NO_2$)-1,2,3,4-tetrahydroisoquinoline (0.88 mmol) and calcium carbonate (70 mg, 0.70 mmole) in EtOH (5 ml) is stirred under refluxing for 15 hours. The reaction mixture is filtered and the filtrate is removed by rotavapor. The residue is purified by chromatography followed by recrystallization in MeOH.

6-{[mono-(5, 6, 7, or 8)-$NO_2$-]1,2,3,4-tetrahydroisoquino-2-yl}purine riboside (Compounds 2, 3, 4, 5, 22). Compound 2: yield 65%; mp 159-160° C.; IR: 3438, 1604, 1528, 1352 cm$^{-1}$; $^1$H NMR (300 MHz, CDCl$_3$) δ 8.15 (1H, s, H-2), 7.86 (1H, d, H-6"), 7.84 (1H, s, H-8), 7.49 (1H, d, H-8"), 7.36 (1H, t, H-7"), 6.53 (1H, br d, OH-2'), 5.81 (1H, d, H-1'), 5.36 (1H, br s, OH-3'), 5.07 (1H, br d, H-2'), 4.53-4.45 (3H, br m, OH-5', H-3', 1"A), 4.35 (1H, s, H-1"B), 3.94 (1H, d, H-4'), 3.76 (2H, br m, H-5'), 3.28 (2H, t, H3" or H4"). Anal. Calcd. For C$_{19}$H$_{20}$N$_6$O$_6$ (428.405): C, 53.27%; H, 4.71%; N, 19.62%. Found: C, 53.14%; H, 4.76%; N, 19.32%. Compound 3: yield 51%; mp 127.5-129.5° C.; MS (ESI) m/z 451 (M+Na)$^+$; IR: 3437, 1593, 1523, 1350 cm$^{-1}$; $^1$H NMR (300 MHz, CD$_3$OD) δ 8.30 (1H, s, H-2), 8.29 (1H, s, H-8), 8.10 (2H, m, H-5", 7"), 7.50 (1H, d, H-8"), 5.98 (1H, d, H-1'), 5.50 (2H, br s, OH-2', 3'), 4.74 (1H, t, OH-5'), 4.58 (3H, br s, H-2', 3', 1"A), 4.32 (1H, q, H-4'), 4.17 (1H, d, H-1"B) 3.89 (1H, q, H-5'A), 3.74 (1H, q, H-5'B), 3.15 (2H, t, H3" or H4"). Anal. Calcd. For C$_{19}$H$_{20}$N$_6$O$_6$·H$_2$O (446.420): C, 51.12%; H, 4.97%; N, 18.82%. Found: C, 51.12%; H, 4.86%; N, 18.36%. Compound 4: yield 61%; mp 172-173° C.; IR: 3422, 1597, 1531, 1346 cm$^{-1}$; $^1$H NMR (300 MHz, CDCl$_3$) δ 8.18 (1H, s, H-2), 8.08 (1H, s, H-8"), 8.02 (1H, d, H-6"), 7.81 (1H, s, H-8), 7.29 (1H, d, H-5"), 6.46 (1H, br d, OH-2'), 5.81 (1H, d, H-1'), 5.46 (1H, br s, OH-3'), 5.07 (1H, q, H-2'), 4.60-4.47 (3H, br m, OH-5', H-3', 1"A), 4.35 (1H, s, H-1"B), 3.94 (1H, d, H-4'), 3.76 (1H, br t, H-5'A), 3.61 (1H, br d, H-5'B), 3.10 (2H, t, H3" or H4"). Anal. Calcd. For C$_{19}$H$_{20}$N$_6$O$_6$ (428.405): C, 53.27%; H, 4.71%; N, 19.62%. Found: C, 53.21%; H, 4.82%; N, 19.42%. Compound 5: yield 66%; mp 148-149° C.; MS (ESI) m/z 451 (M+Na)$^+$; IR: 3370, 1590, 1530, 1343 cm$^{-1}$; $^1$H NMR (300 MHz, CD$_3$COCD$_3$) δ 8.26 (1H, s, H-2), 8.25 (1H, s, H-8), 7.94 (1H, d, H-7"), 7.60 (1H, d, H-5"), 7.47 (1H, t, H-6"), 5.95 (1H, d, H-1'), 5.78 (1H, br s, OH-2'), 5.63 (1H, d, OH-3'), 4.90 (1H, m, H-2'), 4.64 (2H, br m, OH-5', H-3'), 4.37 (2H, q, H-4', 1"A), 4.17 (1H, s, H-1"B), 3.84 (1H, m, H-5'A), 3.71 (1H, m, H-5'B), 3.21 (2H, t, H3" or H4"). Compound 22: yield 95%; mp 157.5-159° C.; IR: 3413, 1600 cm$^{-1}$; $^1$H NMR (300 MHz, DMSO-d$_6$) δ 8.45 (1H, s, H-2), 8.29 (1H, s, H-8), 7.20 (4H, m, H-5", 6", 7", 8"), 5.92 (1H, d, H-1'), 6.47-5.18 (4H, br m, OH-2', 5', 3',H-2'), 4.57 (2H, br m, H-3', 1"A), 4.14 (1H, q, H-4'), 3.96 (1H, s, H-1"B), 3.67 (1H, m, H-5'A), 3.56 (1H, m, H-5'B), 3.93 (2H, t, H3" or H4").

5-$NO_2$-1,2,3,4-tetrahydroisoquinoline (6). To a solution of 11 (500 mg, 2.85 mmole) in acetic acid (50 ml) is added small portions of NaBH$_4$ until TLC examination of the reaction mixture indicating the absence of the starting material. The solution is poured onto ice, basified with NH$_3$·H$_2$O and then extracted three times with CH$_2$Cl$_2$. The organic layer is washed once with water, dried over sodium sulfate and evaporated. The residue is purified by chromatography; (450 mg, yield 90%); $^1$H NMR (300 MHz, CDCl$_3$) δ 7.80 (1H, t, H-7), 7.28 (2H, d, H-6.8), 4.11 (2H, s, ArCH$_2$N), 3.17 (2H, t, ArCH$_2$CH$_2$N), 3.10 (2H, t, ArCH$_2$CH$_2$N).

7-$NO_2$-1,2,3,4-tetrahydroisoquinoline (8). An ice-cold solution of 12 (10.8 g, 80 mmol) in concentrated sulfuric acid (40 ml) is treated with potassium nitrate (8.8 g, 87 mmol) in small portions, keeping the temperature below 5° C. The reaction is left overnight at room temperature and poured onto ice. The resulting solution is basified with NH$_3$·H$_2$O, extracted with CH$_2$Cl$_2$ and concentrated to dryness. The crude product obtained is converted to the hydrochloride salt. Crystallization from methanol gave 8.5 g of the hydrochloride (yield 50%), which is basified to give compound 8. $^1$H NMR (300 MHz, CDCl$_3$) δ 7.98 (1H, d, H-6), 7.91 (1H, s, H-8), 7.24 (1H, d, H-5), 4.10 (2H, s, H-1), 3.17 (2H, t, H-3), 2.89 (2H, t, H-4).

N-acetyl-7-nitro-1,2,3,4-tetrahydroisoquinoline (13). A mixture of 8 (5.4 g, 26 mmol), Et$_3$N (9.8 ml, 70 mmol) and acetic anhydride (5.0 ml, 5 µmol) in CH$_2$Cl$_2$ (70 ml) is stirred at reflux temperature for 1 hour, cooled, and the reaction mixture is poured onto ice. The resulting solution is extracted three times with methylene chloride. The organic layer is dried over sodium sulfate and evaporated in vacuo. The residue is chromatographed on flash silica gel to give 5.3 g of 13 (94% yield). $^1$H NMR (300 MHz, CDCl$_3$) δ 8.05-8.03 (2H, m, H-6,8), 7.43-7.30 (1H, m, H-5), 4.83 (1.2H, s, ArCH$_2$N), 4.72 (0.8H, s, ArCH$_2$N), 3.87 (0.8H, t, ArCH$_2$CH$_2$N), 3.74 (1.2H, t, ArCH$_2$CH$_2$N), 3.02 (1.2H, t, ArCH$_2$CH$_2$N), 2.95 (0.8H, t, ArCH$_2$CH$_2$N), 2.21 (1.2H, s, COCH$_3$), 2.20 (1.8H, s, COCH$_3$).

N-acetyl-7-amino-1,2,3,4-tetrahydroisoquinoline (14). A mixture of 13 (5.1 g, 23 mmol), activated carbon (4.2 g), ferric chloride hexahydrate (2.1 g, 7.6 mmol) and methanol (140 ml) is stirred under refluxing for 20 minutes. To the boiling mixture is added hydrazine hydrate (8.5 g, 265 mmol) dropwise, and the mixture is refluxed for an additional 4 h, cooled and filtered and the residue washed with methanol. The filtrate is concentrated in vacuo and the residue recrystallized from EtOAc to give compound 14 (3.8 g, 85% yield). $^1$H NMR [300 MHz, (CD$_3$)$_2$SO], a 3:2 mixture of amide conformers doubling most signals, δ 6.80 (1H, d, H-5), 6.40 (1H, d, H-6), 6.33 (1H, s, H-7), 4.89 (2H, br s, NH$_2$), 4.46 (0.8H, s, ArCH$_2$N), 4.41 (1.2H, s, ArCH$_2$N), 3.57 (2H, t, ArCH$_2$CH$_2$N), 2.66 (1.2H, t, ArCH$_2$CH$_2$N), 2.55 (0.8H, t, ArCH$_2$CH$_2$N), 2.06 (1.2H, s, COCH$_3$), 2.05 (1.8H, s COCH$_3$).

N-acetyl-7-trifluoroacetamido-1,2,3,4-tetrahydroisoquinoline (15). A solution of 14 (3.0 g, 17 mmol), trifluoroacetic acid (2 ml, 28 mmol) and trifluoroacetic anhydride (4 ml, 28 mmol) in CH$_2$Cl$_2$ is refluxed for 15 minutes, cooled, and the mixture is poured onto ice, extracted twice with CH$_2$Cl$_2$ and evaporated. The mixture is chromatographed on silica gel to give 4.5 g of compound 15 (94% yield). $^1$H NMR [300 MHz, (CD$_3$)$_2$SO], a 3:2 mixture of amide conformers doubling most signals, δ 11.24 (0.8H, s, NH), 11.21 (1.2H, s, NH), 7.55-7.40 (2H, m, H5.8), 7.22 (0.6H, s, H-6), 7.20 (0.4H, s, H-6), 4.64 (0.8H, s, ArCH$_2$N), 4.57 (1.2H, s, ArCH$_2$N), 3.65 (2H, t, ArCH$_2$CH$_2$N), 2.84 (1.2H, t, ArCH$_2$CH$_2$N), 2.73 (0.8H, t, ArCH$_2$CH$_2$N), 2.06 (1.2H, s, COCH$_3$), 2.05 (1.8H, s COCH$_3$).

N-acetyl-7-trifluoroacetamido-6 (8)-nitro-1,2,3,4-tetrahydroisoquinoline (16,17) and N-acetyl-7-amino-6 (8)-nitro-1,2,3,4-tetrahydroisoquinoline (18,19). Compound 15 (4.5 g, 16 mol) is dissolved in 30 ml ice-cold concentrated H$_2$SO$_4$. To this solution is added powdered potassium nitrated (2 g, 20 mmol) portionwise, keeping the temperature around 4° C. The mixture is stirred at 0° C. overnight, and then poured onto ice. The resulting solution is basified with ammonium hydroxide, and extracted twice with $CH_2Cl_2$. The organic layer is dried over sodium sulfate and concentrated to dryness. The product is a mixture of compounds 16 and 17 (as determined by $^1HNMR$). Hydrolysis of compounds 16 and 17 in MeOH (60 ml) and concentrated HCl (15 ml) at refluxing temperature for 50 min followed by evaporation, basification with ammonium hydroxide and then extracted with $CH_2Cl_2$.

The organic layer is dried over $Na_2SO_4$ and evaporated, the crude product is chromatographed on silica gel to give 1.1 g of compound 18 and 0.5 g of compound 19, 30 and 15% yields, respectively. Compound 16: MS (ESI) m/z 354 $(M+Na)^+$, m/z 330 $(M-H)^-$; $^1H$ NMR (300 MHz, $CDCl_3$), a 3:2 mixture of amide conformers doubling most signals, δ 11.38 (0.4H, s, NH), 11.32 (0.6H, s, NH), 8.56 (1H, s, H-5), 8.15 (0.4H, s, H-8), 8.13 (0.6H, s, H-8), 4.86 (1.2H, s, $ArCH_2N$), 4.74 (0.8H, s, $ArCH_2N$), 3.88 (0.8H, t, $ArCH_2CH_2N$), 3.74 (1.2H, t, $ArCH_2CH_2N$), 2.99 (1.2H, t, $ArCH_2CH_2N$), 2.93 (0.8H, t, $ArCH_2CH_2N$), 2.21 (3H, s, $COCH_3$). Compound 17: MS (ESI) m/z 354 $(M+Na)^+$, m/z 330 $(M-H)^-$; $^1H$ NMR (300 MHz, $CDCl_3$), a 3:2 mixture of amide conformers doubling most signals, δ 9.64 (1H, br s, NH), 8.21 (0.4H, d, H-5), 8.18 (0.6H, d, H-5), 7.46 (0.4H, d, H-6), 7.43 (0.6H, d, H-6), 4.89 (1.2H, s, $ArCH_2N$), 4.75 (0.8H, s, $ArCH_2N$), 3.86 (0.8H, t, $ArCH_2CH_2N$), 3.78 (1.2H, t, $ArCH_2CH_2N$), 3.01 (1.2H, t, $ArCH_2CH_2N$), 2.96 (0.8H, t, $ArCH_2CH_2N$), 2.06 (3H, s, $COCH_3$). Compound 18: MS (ESI) m/z 258 $(M+Na)^+$; $^1H$ NMR (300 MHz, $CDCl_3$), a 2:1 mixture of amide conformers doubling most signals, δ 7.94 (1H, s, H-5), 6.60 (1H, s, H-8), 5.96 (2H, br s, $NH_2$), 4.68 (1.3H, s, $ArCH_2N$), 4.56 (0.7H, s, $ArCH_2N$), 3.80 (0.7H, t, $ArCH_2CH_2N$), 3.67 (1.3H, t, $ArCH_2CH_2N$), 2.85 (1.3H, t, $ArCH_2CH_2N$), 2.79 (0.7H, t, $ArCH_2CH_2N$), 2.18 (3H, s, $COCH_3$); $^{13}C$ NMR δ 169.9 and 169.7 ($COCH_3$), 143.6 and 143.2, 142.5 and 141.5, 131.5 and 131.3, 123.4 and 123.5 (C-6,7,9,10), 126.1 and 125.5, 116.1 and 115.5 (C-5,8), 48.1, 44.4, 44.1, 39.9 (C-1,3), 28.5 and 27.5 (C-4), 22.1 and 21.8 ($COCH_3$). Compound 19: MS (ESI) m/z 258 $(M+Na)^+$, m/z 234 $(M-H)^-$; $^1H$ NMR (300 MHz, $CDCl_3$), a 3:2 mixture of amide conformers doubling most signals, δ 7.10 (0.6H, d, H-5), 7.05 (0.4H, d, H-5), 6.73 (0.6H, d, H-6), 6.68 (0.4H, d, H-6), 5.52 (1.2H, s, $NH_2$), 5.34 (0.8H, s, $NH_2$), 4.93 (0.8H, s, $ArCH_2N$), 4.81 (1.2H, s, $ArCH_2N$), 3.79 (1.2H, t, $ArCH_2CH_2N$), 3.68 (0.8H, t, $ArCH_2CH_2N$), 2.83 (0.8H, t, $ArCH_2CH_2N$), 2.77 (1.2H, t, $ArCH_2CH_2N$), 2.16 (3H, s, $COCH_3$). $^{13}C$ NMR δ 169.5 and 169.2 ($COCH_3$), 142.9 and 142.4, 131.0 and 130.1, 125.7, 124.3 (C-7,8,9,10), 135.4 and 134.5, 117.7 and 117.2 (C-5, 6), 47.3, 43.7, 42.9, 39.1 (C-1, 3), 29.0 and 28.1 (C-4), 22.1 and 21.6 ($COCH_3$).

N-acetyl-6 (8)-nitro-1,2,3,4-tetrahydroisoquinoline (20,21). To a stirred solution of compound 18 (19) (290 mg, 1.23 mmol) in HCl (6M, 4 ml) is added dropwise a solution of $NaNO_2$ (110 mg, 1.6 mmol) in water (0.5 ml) at 0° C. After stirring at 0° C. for 2 h, hypophosphorous acid (50% aqueous solution, 1.4 ml) is added dropwise, and the mixture is stirred at 40° C. for 10 h, then poured into water and extracted with methylene chloride. The organic layer is dried over $NaSO_4$ and evaporated. The crude product is purified by chromatography and afforded compound 20 (21) (233 mg, 86%). Compound 20: MS (ESI) m/z 243 $(M+Na)^+$, m/z 219 $(M-H)^-$; $^1H$ NMR (300 MHz, $CDCl_3$), a 2:1 mixture of amide conformers doubling most signals, δ 8.08-8.03 (2H, m, H-5, 7), 7.31 (1H, d, H-8), 4.83 (1.3H, s, $ArCH_2N$), 4.72 (0.7H, s, $ArCH_2N$), 3.87 (0.7H, t, $ArCH_2CH_2N$), 3.74 (1.3H, t, $ArCH_2CH_2N$), 3.02 (1.3H, t, $ArCH_2CH_2N$), 2.96 (0.7H, t, $ArCH_2CH_2N$), 2.21 (3H, s, $COCH_3$). Compound 21: MS (ESI) m/z 243 $(M+Na)^+$; $^1H$ NMR (300 MHz, $CDCl_3$), a 3:2 mixture of amide conformers doubling most signals, δ 7.97 (0.6H, d, H-7), 7.94 (0.4H, d, H-7), 7.49-7.32 (2H, m, H-6, 5), 5.09 (0.8H, s, $ArCH_2N$), 4.99 (1.2H, s, $ArCH_2N$), 3.86 (1.2H, t, $ArCH_2CH_2N$), 3.75 (0.8H, t, $ArCH_2CH_2N$), 3.03 (0.8H, t, $ArCH_2CH_2N$), 2.98 (1.2H, t, $ArCH_2CH_2N$), 2.21 (1.8H, s, $COCH_3$), 2.19 (1.2H, s, $COCH_3$).

6(8)-nitro-1,2,3,4-tetrahydroisoquinoline (6 and 8). Hydrolysis of 20 (21) (190 mg, 0.86 mmol) in MeOH (6 ml) and concentrated hydrochloride acid (3 ml) at refluxing temperature for 10 h afforded 6(8)-nitro-1,2,3,4-tetrahydroisoquinolines (100 mg, 66%), which are separated by flash silica gel chromatography 6-$NO_2$-1,2,3,4-tetrahydroisoquinoline (20): MS (ESI) m/z 179 $(M+H)^+$; $^1H$ NMR (300 MHz, $CDCl_3$) δ 7.99-7.96 (2H, m, H-5, 7), 7.16 (1H, d, H-8), 4.10 (2H, s, $ArCH_2N$), 3.17 (2H, t, $ArCH_2CH_2N$), 2.90 (2H, t, $ArCH_2CH_2N$). 8-$NO_2$-1,2,3,4-tetrahydroisoquinoline (21): MS (ESI) m/z 179 $(M+H)^+$; $^1H$ NMR (300 MHz, $CD_3OD$) δ 7.80 (1H, d, H-7), 7.44 (1H, d, H-5), 7.33 (1H, t, H-6), 4.16 (2H, s, $ArCH_2N$), 3.07 (2H, t, $ArCH_2CH_2N$), 2.92 (2H, t, $ArCH_2CH_2N$).

N-acetyl-6,8-dinitro-7-trifluoroacetamido-1,2,3,4-tetrahydroisoquinoline: MS (ESI) m/z 399 $(M+Na)^+$, m/z 375 $(M-H)^-$; IR: 3448, 1640, 1647, 1270, 1171 $cm^{-1}$; 1H NMR (300 MHz, DMSO-$d_6$), a 3:1 mixture of amide conformers doubling some signals, δ 7.74 (1H, s, H-5), 4.48 (2H, s, $ArCH_2N$), 3.70 (2H, t, $ArCH_2CH_2N$), 2.90 (1.5H, t, $ArCH_2CH_2N$), 2.78 (0.5H, t, $ArCH_2CH_2N$), 2.07 (2.3H, s, $COCH_3$). 2.07 (0.7H, s, $COCH_3$).

Example 4

Biological Testing

Exemplary compounds are tested to determine their es nucleoside transporter binding ability by a flow cytometric assay (Buolamwini et al., 1994). Human leukemia K562 cells growing in RPMI 1640 medium are washed once and suspended at $1.6 \times 10^6$ cells/ml in phosphate-buffered saline at pH 7.4, and incubated with 5-(SAENTA)-X8-fluorescein (25 nM) in the presence or absence of varying concentrations of test compounds at room temperature for 45 minutes. Flow cytometric measurements for cell-associated fluorescence are then performed with a FACSCalibur (Becton Dickinson, San Jose, Calif.) equipped with a 15 mW-argon laser (Molecular Resources Flow Cytometry Facility, University of Tennessee Health Sciences Center). In each assay, 5,000 cells are analyzed from suspensions of $4 \times 10^5$ cells/ml. The units of fluorescence are arbitrary channel numbers. Percentage (%) of control (i.e. es transporter-specific fluorescence in the presence of SAENTA-fluor without test compounds) is calculated for each sample by the equation below.

$$\% \text{ Control} = \frac{(SF_s)}{(SF_f)} \times 100 \quad \text{Eq. 1}$$

where $SF_s$ is the es transporter-specific fluorescence of test samples, and $SF_f$ is the es transporter-specific fluorescence of the SAENTA-fluor ligand standard.

Figure 1:
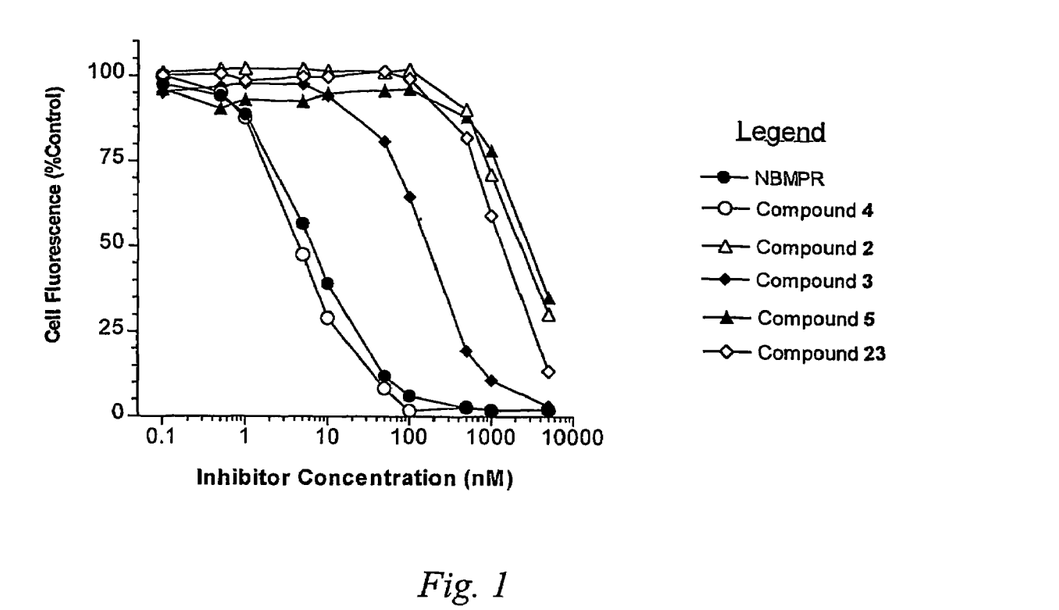
FIG. 1 is a graph showing the equilibrium displacement of SAENTA-fluorescein ligand by of new tetrahydroisoquinoline constrained NBMPR analogs in K562 cells. Cells are incubated with 25 nM SAENTA fluorescein in the presence of inhibitor for 45 minutes at room temperature and analyzed by flow cytometry.

The results are fed into the PRISM program (GraphPad, San Diego, Calif.) to derive concentration-dependent curves using nonlinear regression, as shown in FIG. 1. From these curves, the $IC_{50}$ values are obtained that are used to compare abilities of the new compounds to displace the es transporter-specific ligand (5-(SAENTA)-X8-fluorescein (Buolamwini et al., 1994).

Examples of the present invention (2-5) are tested along with 6-(1,2,3,4-tetrahydroisoquinolinyl)purine riboside (23) as es transporter binding ligands by a facile competitive binding flow cytometric assay using the K562 chronic myelogenous leukemia cell line. The high-affinity es transporter fluorescent ligand, 5-(SAENTA)-X8-fluorescein is used as the competitive ligand to be displaced by the test compounds. Flow cytometry has several advantages over the conventional radioligand binding assays, in that it eliminates radiation hazards and disposal problems, and allows the use of much fewer cells, as few as 5,000 cells compared to 2 million cells per sample for comparable radioligand assays. The compounds of the present invention exhibit a wide range of binding affinities at the es transporter as measured by their ability to displace the es nucleoside transporter-specific ligand, shown by the $K_i$ values in Table 1.

TABLE 1

Flow Cytometrically-Determined $K_i$ Values

| Compound | $K_i$ (nM) |
|---|---|
| 1 (NBMPR) | 0.70 |
| 2 | 250 |
| 3 | 15 |
| 4 | 0.45 |
| 5 | 300 |
| 23 | 150 |

They range from a subnanomolar concentration for compound 4 ($K_i$ 0.45 nM) to high nanomolar concentrations for compounds 2 and 5, at least about a 500 fold difference. The results indicate that, based on known SAR of NBMPR analogs, the compounds of the present invention are as good or even possibly better than the prototype es transporter inhibitor NBMPR. The comparable affinities of compound 4 ($K_i$ 0.45 nM) and NBMPR ($K_i$ 0.70 nM) indicate that conformational changes at this location in the molecules can make a significant difference in binding to the es transporter. The corresponding para compound 3, is tightly bound ($K_i$ 15 nM), but much less so than the compound corresponding to the meta nitro substitution, compound 4 ($K_i$ 0.45 nM). These results offer insights into the bioactive conformation of NBMPR at the 6-position substituent, which is responsible for high affinity binding to the es transporter. The solid state conformation of NBMPR has been determined by X-ray diffraction and a solution conformation has also been determined by NMR. The X-ray structure reveals a syn orientation of the purine system about the glycosidic bond, whereas the solution conformation reveals the preponderance of a high-anti orientation of the purine system about the glycosidic linkage. Conformational space analysis of the novel conformationally constrained analogs reported here will shed light on the bioactive conformation of NBMPR and provide insights for further es transporter inhibitor design.

The es transporter binding high affinity of compound 4, which is at least equivalent in potency to NBMPR is of interest since this compound will be less likely to lose the nitrobenzyl moiety, and should overcome a major disadvantage of NBMPR, which has to do with the in vivo lability of the nitrobenzyl moiety. The nitrobenzyl group of NBMPR is lost in vivo to form the immunosuppressive product mercaptopurine riboside, with a dramatically reduced es transporter affinity (up to a 1000 fold decrease). This lability of the nitrobenzyl group has actually allowed NBMPR to be used as an effective photolabeling agent of the es nucleoside transporter. This has hampered the clinical applications of NBMPR. Therefore preclinical development of the novel compounds 3 and 4, which lock the nitrobenzyl moiety in place, and are likely to prolong in vivo activity compared to NBMPR, is warranted. Compounds 3 and 4 represent the Best Mode.

Example 5

Inhibition of Uridine Uptake

Figure 2:
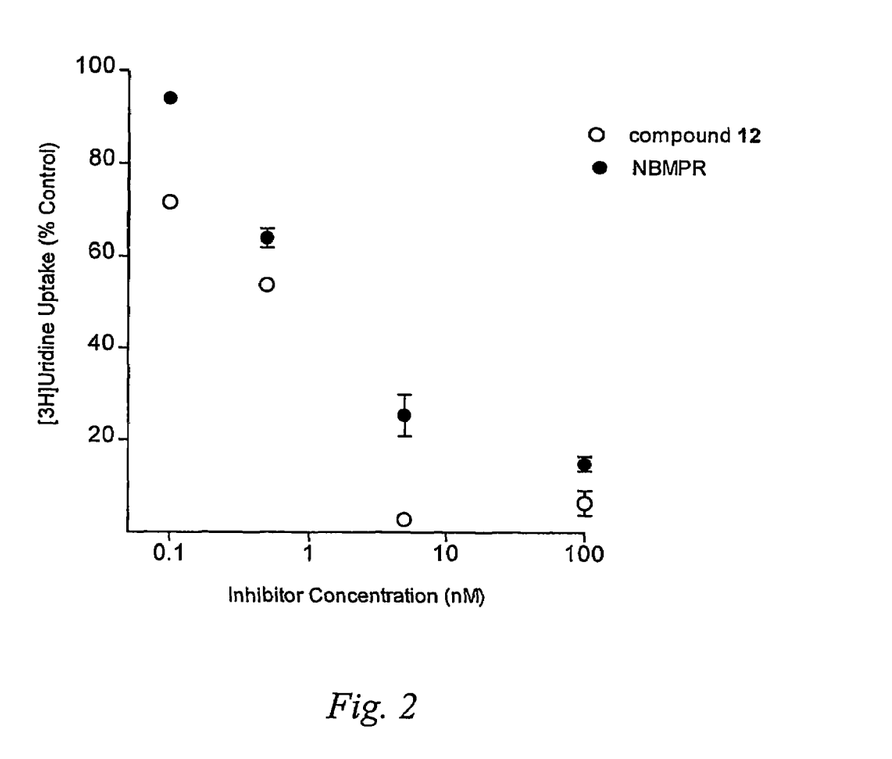
FIG. 2 is a graph showing inhibition of [$^3$H]uridine uptake by NBMPR (•) and a novel tetrahydroisoquinoline analogue compound 12 (○) in JB6 cells. Cells in logarithmic phase of growth are incubated with 1 μM [$^3$H]uridine and 10-second uptake measurements were performed as described in Paterson et al. (1983). The data points are mean ±std for triplicate samples.

Cells in logarithmic phase of growth are incubated with 1 µM [$^3$H]uridine and 10-second uptake measurements are performed as described in Paterson et al. (1983). FIG. 2 indicates that compound 4 potently inhibits the uptake of uridine, a universal nucleoside transporter substrate, better than the prototype standard compound NBMPR, with $IC_{50}$ value in the single digit nanomolar range. These uptake results reflect the flow cytometric binding assay results (see FIG. 1), which show that compound 4 binds very tightly at the es transporter.

Example 7

Heart Treatment During Ischemia

Results shown in Table 2 indicate that both compound 4 and the standard agent NBMPR do enhance the recovery in the rat heart isolated model, indicating that compound 4 is a cardioprotective agent. As shown in Table 2, NBMPR doubles the percentage recovery from control levels, compound 4 triples recovery from control levels. In addition, treatment with compound 4 also appears to keep the heart more relaxed than treatment with either control or NBMPR, an added benefit not seen with the standard agent.

TABLE 2

Effect of Compounds on Rat Heart Recovery from Global Ischemia:

| Heart Treatment during Ischemia and Reperfusion | Recovery from 30 min Global Ischemia (LVDP)$^a$ | Change in EDP$^b$ |
|---|---|---|
| Control (0.02% DMSO) | 12.03 ± 1.7% (n = 6)$^c$ | 66.4 ± 3.0% |
| NBMPR (Standard agent) | 24.40 ± 3.6% (n = 5)$^d$ | 65.2 ± 3.2% |
| Compound 4 (New agent) | 33.60 ± 9.8% (n = 4)$^e$ | 52.5 ± 6.6%$^f$ |

$^a$LVDP = left ventricular developed pressure.
$^b$EDP = end diastolic pressure.
$^c$Data points are the mean SEM, and n is number of animals used.
$^d$Statistically significant at $p < 0.01$.
$^e$Statistically significant at $p < 0.03$.
$^f$Statistically significant in one tail test; $p < 0.04$.

Throughout the disclosure and attachment, various patents and/or publications are referenced, specifically including the lists below. All such patents and/or publications are expressly incorporated herein by reference in their entirety and as such are considered part of this disclosure.

REFERENCES

Abd-Elfattah, A. S., and Wechsler, A. S. (1994). Separation Between Ischemic and Reperfusion Injury by Site Specific Entrapment of Endogenous Adenosine and Inosine Using NBMPR and EHNA. *J. Card. Surg.* 9 (Suppl.), 387-396 and references cited therein Abd-Elfattah, A.-S. A., Hoehner, J. and Wechsler, A. S. (1998a) Identification of Nucleoside Transport Binding Sites in the Human Myocardium. *Mol. Cell. Biochem.* 180, 105-110.

Ajao, J. F. and Bird, C. W. (1985) The Preparation and Oxidative Dimerization of 2-Acetyl-7-hydroxy-1,2,3,4-tetrahydroisoquinoline. A New Approach to Tetrahydroisoquinoline Synthesis. *J. Heterocycl. Chem.* 22, 329-331.

Boumah, C. E., Hogue, D. L. and Cass, C. E. (1992). Expression of High Levels of Nitrobenzylthioinosine-Sensitive Nucleoside Transport in Cultured Human Choriocarcinoma (BeWo) Cells. *Biochem, J.* 288, 987-996

Buolamwini, J. K., Wiley, J. S., Robins, M. J., Craik, J. D., Cass, C. E., Gati, W. P. and Paterson, A. R. P. (1994). Conjugates of fluorescein and SAENTA (5'-S-(2-aminoethyl)-$N^6$-(4-nitrobenzyl)-5'-thioadenosine): Flow Cytometry Probes for the Es Transporter Elements of the Plasma Membrane. *Nucleosides and Nucleotides* 13 (R. K. Robins Memorial Issue), 737-751.

Buolamwini, J. K. (1997). Nucleoside Transport Inhibitors: Structure-Activity Relationships, and Potential Therapeutic Applications. *Curr. Med. Chem.* 4, 35-66.

Cabral, S., Leis, S., Bover, L., Nembrot, M. and Mordoh, J. (1984). Dipyridamole Inhibits the Reversion by Thymidine of Methotrexate Effect and Increases Drug Uptake in Sarcoma 180 Cells. *Proc. Natl. Acad. Sci. USA* 81, 3200-3203

Cass, C. E. (1995). Nucleoside Transport. In *Drug Transport in Antimicrobial and Anticancer Chemotherapy* (Georgopapadakou, N. H., ed.), pp. 403-451, Marcel Dekker, New York Elion, G. B. (1967). Biochemistry and Pharmacology of Purine Analogues. *Fed. Proc.* 26, 898-904

Engler, R. (1987) Consequences of Activation and Adenosine-Mediated Inhibition of Granulocytes During Myocardial Ischemia. *Fed. Proc.* 46, 2407-2412.

Erion, M. D. (1993). Adenosine Receptors as Pharmacological Targets. *Ann. Rev. Med. Chem.* 28, 295-303

Fox, M.; Boyle, J. M.; Kinsella, A. R. (1991). Nucleoside Salvage and Resistance to Antimetabolite Anticancer Agents. *Br. J. Cancer* 64, 428-436

Gati, W. P. and Paterson, A. R. P. (1989). Nucleoside Transport. In *The Red Cell Membrane: Structure, Function, and Clinical Implications* (Agre, P. and Parker, J. C., eds.), pp. 635-661, Marcel Dekker, New York Grem, J. L. and Fischer, P. H. (1985). Augmentation of 5-Fluorouracil Cytotoxicity in Human Colon Cancer Cells by Dipyridamole. *Cancer Res.* 45, 2967-2972

Hoehner, J., Wechsler, A. S., Abd-Elfattah, A.-S. A. (1996) Nucleoside Transport in the Human Kohne, C.-H, Hiddemann, W., Schuller, J., Weiss, J., Lohmann, H.-P., Schmitz-Hubner, U, Bodenstein, H. Schober, C., Wilke, H., Grem, J. and Schmoll, H.-J. (1995). Failure of Orally Administered Dipyridamole to Enhance the Antineoplastic Activity of Fluorouracil in Combination with Leucovorin in Patients with Advanced Colorectal Cancer: A Prospective Randomized Trial. *J. Clin. Oncol.* 13, 1201-1208

Linden, J. (2001) Molecular Approach to Adenosine Receptors: Receptor-Mediated Mechanisms of Tissue Protection. *Ann. Rev. Pharmacol. Toxicol.* 41, 775-787.

Newby, A. C. (1984). Adenosine and the Concept of "Retaliatory Metabolites". *Trend Biochem. Sci.* 9, 42-44

Ohta, A. and Stkovski, M. (2001) The Role of G-Protein-Coupled Adenosine Receptors in Downregulation of Inflammation and Protection from Tissue Damage. *Nature* 414, 916-920

Parkinson, F. E., Zhang, Y. W., Shepel, P. N., Greenway, S. C., Peeling, J. and Geiger, J. D. (2000) Effects of Nitrobenzylthioinosine on Neuronal Injury, Adenosine Levels and Adenosine Receptor Activity in Rat Forebrain Ischemia. *J. Neurochem.* 75:795-802.

Paterson, A. R. P. and Cass, C. E. (1986). Transport of Nucleoside Drugs in Animal Cells. In *Membrane Transport of Antineoplastic Agents* (Goldman, I. D., ed.), pp. 309-329, Pergamon Press, Oxford Paterson, A. R. P., Clanachan, A. S., Craik, J. D., Gati, W. P., Jacobs, E. S., Wiley, J. S. and Cass, C. E. (1991). Plasma Membrane Transport of Nucleosides, Nucleobases and Nucleotides. In *Role of Adenosine and Adenine Nucleotides in the Biological System* (S. Imai and M. Nakazawa, eds.), pp. 133-149, Elsevier, Tokyo Paterson, A. R. P., Jacobs, E. S., Harley, E. R., Fu, N.-W., Robins, M. J. and Cass, C. E. (1983). Inhibition of Nucleoside Transport. In *Regulatory Functions of Adenosine* (Berne, R. M., Rall, T. W. and Rubio, R., eds.), pp. 203-220, Martinus Nijhoff, The Hague Paul, B.; Chen, M. F.; Paterson, A. R. P. (1975). Inhibitors of Nucleoside Transport: Structure-Activity Relationships. *J. Med. Chem.*, 18, 968-973

Phillis, J. W. and O'Regan, M. H. (1996). Effects of Adenosine Deaminase, Deoxycoformycin, and of Nucleoside Transport, Propentophylline, on Post-Ischemic Recovery of Adenine Nucleotides in Rat Brain. *Neurochem. Res.* 21, 347-353

Plagemann, P. G. W., Wohlhueter, R. M. and Woffendin, C. (1988). Nucleoside and Nucleobase Transport in Animal Cells. *Biochim. Biophys. Acta* 947, 405-443

Robins, M. J., Asakura, J.-I., Kanelcu, M., Shibuya, S. Jacobs, E. S., Agbanyo, F. R., Cass, C. E. and Paterson, A. R. P. (1994). Synthesis of Substituted-Benzyl and Sugar-Modified Analogues of 6-N-(4-Nitrobenzyl)adenosine and their Interactions with "ES" Nucleoside Transport Systems. *Nucleosides and Nucleotides* 13, 1627-1646

Rudolphi, K. A., Schubert, P., Parldnson, F. E. and Fredholm, B. B. (1992). Neuroprotective Role of Adenosine in Cerebral Ischemia. *Trends Pharmacol. Sci.* 13, 439-445.

Strachan, T. and Read, A. P. (1996). *Human Molecular Genetics*, pp. 574-576, BIOS Scientific Publishers, Frome, UK Tercel, M., Wilson, W. R., Anderson, R. F. and Denny, W. A. (1996) Hypoxia-Selective Antitumor Agents. 12. Nitrobenzyl Quaternary Salts as bioreductive Prodrugs of the Allcylating Agent Mechlorethamine. *J. Med. Chem.* 39, 1084-1094.

Tew, K. D., Houghton, P. J. and Houghton, J. A (1993). *Preclinical and Clinical Modulation of Anticancer Drugs*, Chap. 7, CRC Press, Boca Raton Thorn, J. A.; Jarvis, S. M. (1996). Adenosine Transporters. *Gen. Pharmacol.*, 27, 613-620

Van Belle, H. (1993a). Nucleoside Transport Inhibition: A Therapeutic Approach to Cardioprotection via Adenosine? *Cardiovasc. Res.* 27, 68-76

Van Belle, H. (1993b). Adenosine Promoters: An Overview of Existing Strategies. *Curr. Opin. Invest. Drugs* 2, 1191-1199.

Ver Donck, K. (1994). Purine Metabolism in the Heart: Strategies for Protection Against Myocardial Ischemia. *Pharm. World. Sci.* 16, 69-76

Williams, E. F. Radioreceptor Characterization of Cardiovascular Nucleoside Transporters. *SAAS Bulletin: Biochem. & Biotech.* 9, 51-56 (1996).

Young, J. D., Cheeseman, C. I., Mackey, J. R., Cass, C. E. and Baldwin, S. A. (2000) Molecular Mechanisms of Nucleoside and Nucleoside Drug Transport. In *Current Topics in Membranes*, Vol. 50, Barrett, K. E. and Donowitz, M., eds., Academic Press, San Diego, Calif., pp. 329-378

Young, J. D., Jarvis, S. M., Robins, M. J. and Paterson, A. R. P. (1983) Photoaffinity Labeling of the Human Erythrocyte Nucleoside Transporter By $N^6$-(P-Azidobenzyl)Adenosine And Nitrobenzylthioinosine. Evidence that the Transporter is a Band 4.5 Polypeptide. *J. Biol. Chem.* 258, 2202-2208.

Zhang, Y. W., Shepel, P. N., Peeling, J., Geiger, J. D. and Parkinson, F. E. (2002). Effects of Nitrobenzylthioinosine on adenosine levels and neuronal injury in Rat Forebrain Ischemia. *Neurosci. Res. Commun.* 30, 83-89.

The following patents relate to the field of nucleoside transport inhibitors within the scope of certain embodiments of the present invention, and are incorporated herein by reference:

U.S. Pat. No. 6,455,507 Benzimidazole derivatives;

U.S. Pat. No. 6,455,506 Lyxofuranosyl benzimidazoles as antiviral agents;

U.S. Pat. No. 6,423,829 Nitrobenzylmercaptopurineriboside (NBMPR)-insensitive, equilibrative, nucleoside; transport protein, nucleic acids encoding the same and methods of use;

U.S. Pat. No. 6,413,938 Benzimidazole derivatives for the treatment of viral infections;

U.S. Pat. No. 6,403,589 Method of treating pain with draflazine-analogues;

U.S. Pat. No. 6,350,753 2-Substituted-4-substituted-1,3-dioxolanes and use thereof;

U.S. Pat. No. 6,342,501 Pyrrolo[2,3-d]pyrimidines as antiviral agents;

U.S. Pat. No. 6,319,946 Inhibitors of aspartyl protease;

U.S. Pat. No. 6,307,043 Benzimidazole and its ribonucleoside;

U.S. Pat. No. 6,297,250 Pyrimidopyrimidine compounds;

U.S. Pat. No. 6,225,460 Nucleotide analogs;

U.S. Pat. No. 6,180,639 1,3-oxathiolane nucleoside analogues;

U.S. Pat. No. 6,177,435 Therapeutic combinations;

U.S. Pat. No. 6,156,737 Use of dideoxy nucleoside analogues in the treatment of viral infections;

U.S. Pat. No. 6,096,786 Immunopotentiatory agent and physiologically acceptable salts thereof;

U.S. Pat. No. 5,998,605 Antiviral benzimidazole nucleoside analogues and method for their preparation;

U.S. Pat. No. 5,977,061 $N_6$-substituted nucleotide analogues and their use;

U.S. Pat. No. 5,958,980 Immunopotentiatory agent and physiologically acceptable salts thereof;

U.S. Pat. No. 5,922,696 Ethylenic and allenic phosphonate derivatives of purines;

U.S. Pat. No. 5,905,082 Crystalline oxathiolane derivatives;

U.S. Pat. No. 5,886,179 Nucleotide analogs;

U.S. Pat. No. 5,872,151 Immunopotentiatory agents and physiologically acceptable salts thereof;

U.S. Pat. No. 5,817,647 Unsaturated acetylene phosphonate derivatives of purines;

U.S. Pat. No. 5,798,340 Nucleotide analogs;

U.S. Pat. No. 5,767,100 Compounds and methods for making and using same;

U.S. Pat. No. 5,750,729 Compounds and methods for malting and using same;

U.S. Pat. No. 5,717,095 Nucleotide analogs;

U.S. Pat. No. 5,693,771 Methods for making nucleoside analogs;

U.S. Pat. No. 5,681,581 Controlled release pharmaceutical formulations of 3'-azido-3'-deoxythymidine and methods of use;

U.S. Pat. No. 5,670,520 Method for inhibiting virus replication in mammalian cells using carbostyil derivatives;

U.S. Pat. No. 5,663,154 2',3'-dideoxy-3'-fluoro-purine ribonucleosides;

U.S. Pat. No. 5,659,023 Nucleotide analogues;

U.S. Pat. No. 5,656,745 Nucleotide analogs;

U.S. Pat. No. 5,618,820 1,3-oxathiolane nucleoside analogues and methods for using same;

U.S. Pat. No. 5,607,929 Antiviral dibenzothiazepinone derivatives;

U.S. Pat. No. 5,589,474 Dibenzothiazepinthione as antiviral agents;

U.S. Pat. No. 5,587,480 Substituted 1,3-oxathiolanes and substituted 1,3-dithiolanes with antiviral properties;

U.S. Pat. No. 5,574,149 Method of treating HIV infections with 2',3'-dideoxy-3'-fluoro-5-chlorouridine;

U.S. Pat. No. 5,547,976 Further indole derivatives with antiviral activity;

U.S. Pat. No. 5,538,975 1,3-oxathiolane nucleoside compounds and compositions; and U.S. Pat. No. 5,508,310 Immunopotentiatory agents and physiologically acceptable salts thereof U.S. Pat. No. 5,504,093 Method for inhibiting nucleoside and nucleobase transport in mammalian cells, and method for inhibition of DNA virus replication U.S. Pat. No. 5,491,135 Compositions of N-(phosphonoacetyl)-L-aspartic acid and methods of their use as broad spectrum antivirals It will be apparent to one of ordinary skill in the art that various modifications and variations can be made in the present invention without departing from the spirit and scope of the invention. Other embodiments of the invention will be apparent to those skilled in the art from consideration of the specification and practice of the invention disclosed herein. The above examples and preferred embodiments are for exemplary purposes, and not intended to limit the spirit and scope of the present invention.

Unless otherwise indicated, all numbers expressing quantities of ingredients, properties such as reaction conditions, and so forth used herein are to be understood as being modified in all instances by the term "about." Accordingly, unless indicated to the contrary, the numerical parameters set forth herein are approximations that may vary depending upon the desired properties sought to be determined by the present invention.

Notwithstanding that the numerical ranges and parameters setting forth the broad scope of the invention are approximations (particularly in the disclosure, above), the numerical values set forth in the disclosure/experimental or example sections are reported as precisely as possible. Any numerical value, however, inherently contain certain errors necessarily resulting from the standard deviation found in their respective testing measurements.

I claim:

1. A compound of the following formula, and analogs thereof:

FORMULA II wherein:
R₁ is H, OH, NH₂, N₃, halogen;
R₂ is H, OH, NH₂, N₃, halogen;
R₃ is H, NH₂, substituted amino, halogen;
R₄ is H, OH, NO₂, CN, N₃, NCS, halogen;
R₅ is H, OH, NO₂, CN, N₃, NCS, halogen, halogen-CH₂COCH₃;
R₆ is H, OH, NO₂, CN, N₃, NCS, halogen, halogen-CH₂COCH₃;
R₇ is H, OH, NO₂, CN, N₃, NCS, halogen;
R₈ is H, OH, OCH₃, NO₂, CN, N₃, NCS, halogen, A-Reporter where A is O, S, NH, and the Reporter is a tethered reporter group;
provided that substituents R₄, R₅, R₆, R₇, cannot all be H at the same time if R₁ is H, R₂ is OH, R₃ is H and R₈ is OH.

2. A compound of claim 1, of the following formula, and analogs thereof:

wherein R₁-R₂ are defined as in claim 1.

3. A compound of claim 1, of the following formula, and analogs thereof:

4. A method of inhibiting a nucleoside transporter in a subject in need thereof, comprising:
administering a nucleoside transporter inhibiting amount of a compound of one of claims 2-3, pharmaceutically acceptable acid addition salt, ester, or prodrug thereof of the following formula to the subject.

5. A method of treating heart disease or stroke conditions in a subject in need thereof, comprising:
administering a nucleoside transporter inhibiting amount of a compound of one of claims 2-3, pharmaceutically acceptable acid addition salt, ester, or prodrug thereof of the following formula to the subject.

6. The method of claim 5, wherein the heart disease is ischemic heart disease.

7. A method of treating infectious disease in a subject in need thereof, comprising:
administering a nucleoside transporter inhibiting amount of a compound of one of claims 2-3, pharmaceutically acceptable acid addition salt, ester, or prodrug thereof of the following formula to the subject.

8. The method of claim 7, wherein the infectious disease is a viral infection.

9. The method of claim 7, wherein the infectious disease is an HIV-related disease.

10. The method of claim 7, wherein the infectious disease is a gram-positive bacterial infection.

11. The method of claim 7, wherein the infectious disease is a gram-negative bacterial infection.

12. The method of claim 7, wherein the infectious disease is a fungal infection.

13. The method of claim 7, wherein the infectious disease is a protozoal infection.

* * * * *